United States Patent [19]

Tsatsas et al.

[11] 4,371,538
[45] Feb. 1, 1983

[54] SPIRO DERIVATIVES, PROCESS FOR THEIR PREPARATION AND MEDICATIONS CONTAINING SAME

[75] Inventors: Georges Tsatsas, Athens; Evan E. Costakis, Paraskevi Attikis; Georges V. Foscolos, Piraeus, all of Greece

[73] Assignee: Etablissements Nativelle S.A., Paris, France

[21] Appl. No.: 195,692

[22] Filed: Oct. 9, 1980

[30] Foreign Application Priority Data

Oct. 9, 1979 [FR] France ................. 79 25041

[51] Int. Cl.³ .................. A61K 31/445; C07D 307/94
[52] U.S. Cl. ..................... 424/267; 424/274; 424/279; 424/285; 546/15; 548/407; 549/265; 549/331
[58] Field of Search ............ 546/15; 260/343.6, 347.7, 260/326.5 CA, 326.5 D; 424/279, 285, 267

[56] References Cited

U.S. PATENT DOCUMENTS 2,490,937 12/1949 Weston .............................. 260/343.6
2,960,441 11/1960 Van Wessem et al. ........... 260/343.6

FOREIGN PATENT DOCUMENTS 631328 11/1961 Canada ............................ 260/347.7

*Primary Examiner*—Ethel G. Love

*Attorney, Agent, or Firm*—Sughrue, Mion, Zinn, Macpeak & Seas

[57] ABSTRACT

The invention relates to new derivatives of spiro compounds represented by the general formula (I)

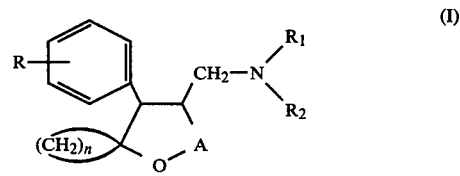

wherein R is a hydrogen atom, a halogen atom, an alkyl group or an alkoxy group; $R_1$ and $R_2$ represent a hydrogen atom or an alkyl group or together form a nitrogen-containing heterocyclic ring; A is a $>CH_2$ group or a $>CO$ group; n is 4 or 5. These compounds can be prepared from β-hydroxyacids by intramolecular rearrangement by the action of a strong acid, in order to form a γ-spirolactone which is converted into an α-carboxy γ-spirolactone to form the compounds of formula (I) using a Mannich reaction. As necessary, a reduction is then carried out. These compounds are useful medically, in particular, as an antidepressant, a stimulant, and a neuroleptic.

8 Claims, No Drawings

SPIRO DERIVATIVES, PROCESS FOR THEIR PREPARATION AND MEDICATIONS CONTAINING SAME

FIELD OF THE INVENTION

The present invention relates to spiro derivatives, and, in particular, aryl-4-aminoalkyl-3 oxa-1 spiroalkanes and aryl-4 aminoalkyl-3 oxa-1 spiroalkanones-2, a process for their preparation, and their application for medical treatment.

SUMMARY OF THE INVENTION

The spiro derivatives of the present invention can be represented by the general formula (I):

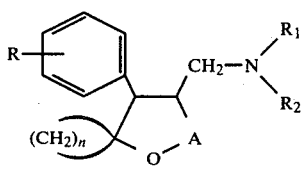

wherein R is a hydrogen atom, a halogen atom, an alkyl group or an alkoxy group; $R_1$ and $R_2$, which may be the same or different, represent a hydrogen atom or an alkyl group, or together form a nitrogen-containing heterocyclic ring; A represents a $>CH_2$ group or a $>CO$ group; and n is 4 or 5.

When $R_1$ and $R_2$ form a nitrogen-containing heterocyclic ring with the nitrogen atom to which they are attached, this heterocyclic ring preferably comprises a 5- or 6-membered ring and can, for example, be a pyrrolyl, a pyrrolidinyl, a piperidinyl or a similar group, etc.

This invention further provides a process for the preparation of the compounds of the general formula (I) starting from β-hydroxyacids of the general formula (II):

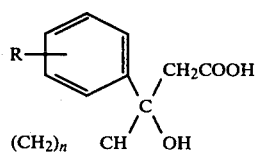

wherein R and n have the same significance as in the formula (I), by the action of a conventional strong acid such as concentrated sulfuric acid, followed by hydrolysis. The reaction takes place by intramolecular rearrangement according to the principle described in G. Tsatas and G. Cottakis *Bull. Soc. Chim. de France*, page 3609 (1970), and thus a γ-spirolactone of the general formula (III) is obtained:

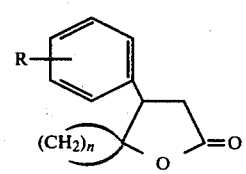

wherein R and n have the definition indicated for the general formula (I).

By the action of magnesium methyl carbonate on the spirolactone of the general formula (III), the corresponding a-carboxy-γ-spirolactone of the general formula (IV) is obtained:

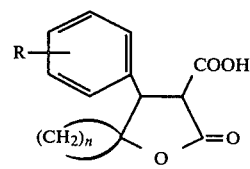

which is transformed into a compound of the general formula (I) of the invention, wherein A represents a $>CO$ group, by action of a suitable aliphatic amine, in the presence of formaldehyde or paraformaldehyde using a Mannich reaction.

The strong acid can be selected from the strong acids conventional in the art, for example, concentrated sulfuric acid, preferably in the presence of oleum, hydrochloric acid, p-toluene sulfonic acid, a super acid or a Lewis acid, etc.

DETAILED DESCRIPTION OF THE INVENTION

According to one embodiment of the process of the present invention, the compounds of the general formula (I), wherein A is $>CH_2$, are preferably obtained starting from compounds of the general formula (I) wherein A is $>CO$, by reductive opening by means of lithium aluminum hydride to form a diol, then cyclization by internal dehydration by the action of p-bromobenzene sulfonyl chloride in pyridine.

The β-hydroxyacids of the general formula (II) used as starting compounds for the preparation of the spiro derivatives of the general formula (I) of the invention, can easily be obtained by known processes, for example by reacting a halogenated ester such as ethyl bromoacetate, with zinc and a suitable cycloalkylarylketone, using a Reformatsky reaction, followed by saponification of the ester obtained.

The invention also covers salts of the spiro derivatives of the general formula (I) and in particular pharmaceutically acceptable acid addition salts, by reaction with conventional acids, such as hydrochloric, sulfuric, phosphoric, acetic, propionic, oxalic, lactic, citric, tartaric, or malonic acids. Salts can also be prepared by reacting an alkyl halide with the spiro compounds of the invention. The salts can be obtained in the usual manner by reacting in largely stoichiometric proportions a spiro derivative of the invention with a suitable acid, in a suitably selected solvent, such as an alcohol, a ketone, a chlorinated solvent, or an ether.

This invention further provides use of the spiro derivatives of general formula (I) and the pharmaceutically acceptable salts thereof as active ingredients in medicaments. Pharmacological and toxicological experiments carried out on the spiro compounds of general formula (I) have indeed revealed interesting properties enabling their application in medical treatment.

Experiments were carried out on rats and mice using the spiro derivatives of the invention in the form of an aqueous suspension in gum arabic, by administering the compounds orally in a volume of 0.1 ml per 10 g of body weight.

The oral toxicity, tested in mice reveals an LD 50 lethal dose on the order of 350 to 400 mg/kg.

The spiro compounds of the present invention are active on the central nervous system. More particularly, they offer antireserpinic and analgesic activity and provide proadrenergic, protryptaminergic, dopaminergic and sedative effects, as indicated below in more detail, taking as a specific example (dimethylaminomethyl)-3 phenyl-4 oxa-1 spiro[4,5]decane, revealing a neuropharmacological profile similar to that of an antidepressant such as imipramine.

Antireserpinic Activity

The product administered after reserpine showed itself capable, at a dose of 25 mg/kg, of partially antagonizing the already existing reserpinic hypothermia and reserpinic palpebral ptosis. This demonstrates activity similar to that of 25 mg/kg of imipramine, administered before the reserpine. It also showed certain antagonistic activity against the hypothermia but this antireserpinic activity remains less than that of imipramine.

Proadrenergic and Protryptaminergic Effects

The potentiating of the toxicity of the amphetamine has been researched in mice. At 25 mg/kg the product showed strong toxicity potentiating activity whereas imipramine is inactive.

On the test for potentiating of the toxicity of yohimbine in mice, the product at 5 mg/kg showed itself more active than tricyclic antidepressants (imipramine and amitryptiline).

Dopaminergic Effects

On testing of catalepsy induced in rats by a neuroleptic (prochlorperazine), the product showed good anticataleptic activity lasting longer than that of an identical dose of imipramine (50 mg/kg), but like imipramine, the molecule does not influence the stereotypies caused by L-dopa in mice whereas the amphetamine and the phenelzine potentiate them strongly but less than that of the phenelzine.

Sedative Effects

The narcosis induced in mice by pentobarbital sodium is greatly prolonged after administration of 50 mg/kg of the compound of the invention. This activity is greater than that of imipramine or phenelzine.

Anticonvulsive Activity

As opposed to tricyclic antidepressants, the compound of this invention under study showed itself to be practically inactive on maximal electroshock or on convulsions induced in mice by cardiazole.

Analgesic Activity

Analgesic action was sought:

A — in the heating plate test which revealed for the product at 50 mg/kg narcotic type central activity comparable to that of codeine. None of the psychotropic products already cited possess similar activity.

B — on the reduction of the number of painful abdominal stretchings caused by the i.p. injection of phenylbenzoquinone in mice, the analgesic activity of the compound of this invention is comparable to a reference analgesic, aspirin, and to that of amitryptiline or an amphetamine.

The compounds of the invention also show considerable anticholinergic activity at the central and peripheral levels verified at doses of 25 mg/kg and 50 mg/kg in mice.

The spiro compounds of the invention also possess antiarrhythmic activity verified on isolated guinea-pig auricle and on the arrhythmias induced by aconitine.

The above-indicated pharmacological properties show that the spiro compounds of the invention can be applied in medical treatment in humans, as therapeutics, especially for the treatment of cerebral disfunctions such as depression states, in the usual fields of application of neuroleptics, antidepressants and stimulants. They can also be used for the treatment of cardiac diseases due to their antiarrhythmic activity.

The new spiro compounds of the invention can be administered in the usual forms containing a pharmacologically effective quantity of the compound as an active ingredient, along with pharmacologically usable supports, for example in the form of tablets, gelules, capsules, pills, suppositories, injectable solutions or syrups.

Tablets can for example be obtained by mixing the spiro compound or one of its salts, as an active ingredient, with solid diluents, such as lactose, mannitol, sorbitol, starch, polyvinylpyrrolidone, magnesium or aluminum stearate, cellulose powder, colloidal silica, talc, etc.

Tablets, and pills, can be prepared by coating so as to form several layers in accordance with known techniques. So as to obtain a delay effect, a coating of one or several layers of a usual product such as carboxymethylcellulose acetophthalate or polyvinyl acetate, etc., can be used.

Injectable solutions can be prepared by means of diluents such as bidistilled water, propylene glycol, a dilute alcoholic solution, or a mixture of these diluents, preferably in the presence of an appropriate preservative selected from those commonly used in the art.

Orally administrable forms can also be prepared, for example, as solutions containing the spiro compound of the invention dissolved in water and glycerol, in the presence of a sweetening agent and an antioxidant.

All formulations adapted to the various methods of administration, oral, parenteral, or rectal, can be used, the compound being associated as an active ingredient with appropriate pharmaceutically acceptable excipients.

The useful dosage can vary according to the subject being treated, age of the subject, the gravity of the disease in question, and the method of administration. As an example, it can be on the order of 0.5 mg to 20 mg per dose, and from 0.5 mg to 90 mg per day approximately, in adult man, for oral administration.

The following examples are given to illustrate the invention without limiting the scope thereof.

EXAMPLE 1

(Dimethylaminomethyl)-3 phenyl-4 oxa-1 spiro[4,4]-nonane-one-2

To a mixture of 80 ml of sulfuric acid and 3 ml of oleum ($H_2S_2O_7$) was added in small quantities, under agitation and by cooling, 33 g of β-cyclopentyl-β-hydroxy-hydrocinnamic acid prepared by heating a mixture of cyclopentylphenylketone, ethyl bromo-acetate and zinc, and by saponifying the ester obtained with potash. The complex formed was agitated at 0° C. for 30 minutes, then hydrolyzed by adding 300 ml of cold water drop by drop.

The mixture obtained was extracted with ether, the ether layers were washed with water and with 10% sodium carbonate, then dried on sodium sulfate. After elimination of the ether by distillation under reduced pressure, the residue was distilled and 27.3 g (yield 90%) of phenyl-4 oxa-1 spiro[4,4]nonane-one-2 was obtained, the structure of which was confirmed by analysis.

13 g of phenyl-4 oxa-1 spiro[4,4]nonane-one-2 was mixed with 200 ml of a solution of methyl carbonate magnesium in dimethylformamide with a magnesium content of 0.12 g per 2.5 ml of solution. The mixture was boiled for 12 hours in a carbon dioxide atmosphere, and after cooling at room temperature was poured under brisk agitation into 400 to 500 g of a mixture of water and ice. A solution of 10% hydrochloric acid was then added slowly and under cooling until the acid reaction and this was left to stand overnight at 0° C.

The solid product which was formed was collected by filtration, and treated over a water bath with a solution of 10% sodium carbonate. The reaction mixture was washed several times with clear water so as to eliminate the noncarboxylated spirolactone. After acidification with a solution of 10% hydrochloric acid, under agitation and by cooling, the mixture was left to stand overnight at 0° C. The solid product thus formed was filtered, washed with water, and vaccum dried with $P_2O_5$.

After recrystallization in a mixture of anhydrous benzene and petroleum ether, 14.8 g (yield 95%) of phenyl-4 oxo-2 oxa-1 spiro[4,4]nonane carboxylic-3 acid was obtained, with a melting point=148°–150° C. (decomposition).

21 g of the acid obtained as above was treated under cooling with 56 ml of an alcoholic solution of 33% dimethylamine, then 13 ml of 35% formaldehyde was added drop by drop, under agitation and cooling. The mixture obtained was agitated at room temperature for 48 hour, then boiled for 1 hour. After evaporation of the solvents under reduced pressure, a residue was obtained to which water was added. The mixture was extracted with ether, then the ether layers were washed with water, with a solution of 5% sodium carbonate, and dried on sodium sulfate. After recrystallization in a mixture of ether and n-pentane, 17.7 g of (dimethylaminomethyl)-3 phenyl-4 oxa-1 spiro[4,4]nonane-one-2 was obtained, with a melting point=76°–77° C. (yield 81%).

Analysis: $C_{17}H_{23}NO_2$ (273.362). Calculated %: C: 74.69, H: 8.48, N: 5.12. Found %: C: 74.44, H: 8.30, N: 4.93.

The structure of the product was confirmed by IR and NMR spectra.

EXAMPLE 2

(Dimethylaminomethyl)-3 phenyl-4 oxa-1 spiro[4,5]decane-one-2

The same process was used as for Example 1 replacing the β-cyclopentyl-β-hydroxy-hydrocinnamic acid with β-cyclohexyl-β-hydroxy-hydrocinnamic acid. During hydrolysis of the complex a viscous product was formed which was crystallized by cooling and friction. After filtration, washing in water and in n-pentane, drying with $P_2O_5$ and recrystallization in a mixture of ether and n-pentane, phenyl-4-oxa-1 spiro[4,5]decane-one-2 was obtained with a yield of 99% and a melting point=104°–105° C.

The spirolactone thus obtained was treated as indicated in Example 1 with a solution of magnesium methyl carbonate in dimethylformamide, by boiling. Thus, phenyl-4 oxo-2 oxa-1 spiro[4,5]decane carboxylic-3 acid was obtained with a yield of 86% and a melting point=158°–160° C. (decomposition).

The acid thus obtained was treated, as indicated in Example 1 with an alcoholic solution of dimethylamine, and (dimethylaminomethyl)-3 phenyl-4 oxa-1 spiro[4,5]-decane-one-2 was obtained, with a yield of 91% and a melting point =117°–119° C.

Analysis: $C_{18}H_{25}NO_2$ (287.368). Calculated %: C: 75.22, H: 8.77, N: 4.87. Found %: C: 75.48, H: 8.67, N: 5.04.

The hydrochloride was prepared by the usual methods, by adding an ethanolic hydrochloric acid solution to a ether solution of the base. The hydrochloride had a melting point =206°–207° C.

Analysis: $C_{18}H_{26}ClNO_2$ (323.853). Calculated %: C: 66.75, H: 8.09, Cl: 10.95, N: 4.33. Found %: C: 66.36, H: 7.83, Cl: 11.30, N: 4.23.

EXAMPLE 3

(Dimethylaminomethyl)-3 (p-tolyl)-4 oxa-1 spiro[4,5]decane-one-2

Using the same process as for Example 1, but replacing the β-cyclopentyl-β-hydroxy-hydrocinnamic acid with p-methyl-β-cyclohexyl-β-hydroxy-hydrocinnamic acid, (p-tolyl)-4 oxa-1 spiro[4,5decane-one-2 was obtained, with a yield of 92% and a melting point=92°–93° C.

The spirolactone thus obtained was treated as indicated in Example 1 with a solution of magnesium methyl carbonate in dimethylformamide, by boiling the mixture. Thus (p-tolyl)-4 oxo-2 oxa-1 spiro[4,5]decane carboxylic-3 acid was obtained with a yield of 79% and a melting point =171°–172° C. (decomposition).

The acid obtained as indicated above was treated under cooling with an alcoholic solution of dimethylamine as indicated in Example 1. Thus, (dimethylaminomethyl)-3 (p-tolyl)-4 oxa-1 spiro[4,5]decane-one-2 was obtained, with a yield of 60% and a melting point=133°–134° C.

Analysis: $C_{19}H_{27}NO_2$ (301.414). Calculated %: C: 75.71, H: 9.03, N: 4.65. Found %: C: 75.76, H: 9.07, N: 4.65.

The hydrochloride of the above compound had a melting point of=221°–222° C.

Analysis: $C_{19}H_{28}ClNO_2$ (337.879). Calculated %: C: 67.54, H: 8.35, Cl: 10.19, N: 4.15. Found %: C: 67.28, H: 8.11, Cl: 10.29, N: 4.44.

EXAMPLE 4

(Dimethylaminomethyl)-3 phenyl-4 oxa-1spiro[4,4]nonane-one-2 iodomethylate 5.5 g of (dimethylaminomethyl)-3 phenyl-4 oxa-1 spiro[4,4]nonane-one-2 obtained as indicated in Example 2 was agitated for 72 hours at room temperature in the presence of 6 ml of methyl iodide in 60 ml of anhydrous acetone. A further 2 ml of methyl iodide was added and the mixture was boiled for 3 hours. After cooling at room temperature, anhydrous ether was added. The salt formed was filtered and recrystallized in a mixture of ethanol and anhydrous ether.

7.7 g of iodomethylate was thus obtained (yield 93%) with a melting point=185°–186° C.

Analysis: $C_{18}H_{26}INO_2$ (415.306). Calculated %: C: 52.05, H: 6.31, I: 30.56, N: 3.37. Found %: C: 51.67, H: 6.37, I: 30.62, N: 3.55.

EXAMPLE 5

(Dimethylaminomethyl)-3 phenyl-4 oxa-1 spiro[4,5]decane-one-2 iodomethylate

Using the process of Example 4 and the spirolactone obtained as indicated in Example 2, the iodomethylate was thus obtained, with a yield of 94% and a melting point =218°-220° C.

Analysis: $C_{19}H_{28}INO_2$ (429.332). Calculated %: C: 53.15, H: 6.57, I: 29.56, N: 3.26, Found %: C: 53.18, H: 6.53, I: 29.50, N: 3.42.

EXAMPLE 6

(Dimethylaminomethyl)-3 phenyl-4 oxa-1 spiro[4,5]decane 17 g of (dimethylaminomethyl)-3 phenyl-4 oxa-1 spiro[4,5]decane-one-2, in solution in 150 ml of anhydrous ether, was added slowly and under agitation to a suspension of 5 g of lithium aluminum hydride in 300 ml of anhydrous tetrahydrofuran and then the mixture was boiled for 7 hours. The complex which formed was hydrolyzed while cold under agitation by adding water and a 10% solution of soda drop by drop. After filtration of the lithium and aluminum hydroxides, the solvents were evaporated under reduced pressure, and the residue which was solidified by cooling was recrystallized in a mixture of ether and n-pentane.

(Phenyl-1 dimethylaminomethyl-2 hydroxy-3) propyl-1 cyclo-hexanol was thus obtained with a yield of 87% and a melting point=146°-147° C.

The amino-diol obtained as indicated above was put in a solution of 300 ml of anhydrous pyridine and 10.4 g of b-bromobenzene sulfonyl chloride was added thereto in small successive quantities under agitation and cooling. The mixture was agitated for 20 hours at room temperature, then poured into water. It was extracted with chloroform and the chloroform layers were washed with water and then dried with sodium sulfate. The solvent was eliminated under a vacuum and the residue was submitted to neutral alumina column chromatography (1 g of residue for 30 g of alumina), using ether as the eluent. After evaporation of the corresponding fractions and purification by recrystallization in a mixture of ether and n-pentane, (dimethylaminomethyl)-3 phenyl-4 oxa-1 spiro[4,5]decane was obtained with a yield of 78% and a melting point of=65° C.

Analysis: $C_{18}H_{27}NO$ (273.404). Calculated %: C: 79.07, H: 9.95, N: 5.12. Found %: C: 79.14, H: 10.14, N: 5.01.

The corresponding hydrochloride, with a melting point of 201°-202° C., was prepared in the usual manner.

Analysis: $C_{18}H_{28}ClNO$ (309.869). Calculated %: C: 69.76, H: 9.11, Cl: 11.44, N: 4.52. Found %: C: 69.79, H: 8.79, Cl: 11.36, N: 4.47.

EXAMPLE 7

(Dimethylaminomethyl)-3 p-chlorophenyl-4 oxa-1 spiro[4,4]-nonane-one-2

This product was obtained by the same process as in Example 1, taking as the starting compound cyclopentyl-p-chlorophenyl ketone (described in Belgian Pat. No. 634,208) in place of cyclopentylphenyl ketone. Thus β-cyclopentyl β-hydroxy chloro-4' hydrocinnamic acid was formed which was converted into p-chloro-phenyl-4 oxa-1 spiro [4,4] nonane-one-2.

After formation of the corresponding acid (MP=153°-155° C.) as indicated in Example 1, dimethylamine in solution in alcohol, in the presence of formaldehyde, was used to obtain the desired compound.

Melting point=92-94° C. (ether/n-pentane).

EXAMPLE 8

(Dimethylaminomethyl)-3 p-chlorophenyl-4 oxa-1 spiro[4,4]-nonane hydrochloride

Using the process of Example 6 but replacing the (dimethylaminomethyl)-3 phenyl-4 oxa-1 spiro[4,5decane-one-2 with (dimethylaminomethyl)-3 p-chlorophenyl-4 oxa-1 spiro-[4,4]nonane-one-2, which was added slowly to a suspension of lithium aluminum hydride in anhydrous tetrahydrofuran.

The amino-diol obtained was transformed into (dimethylaminomethyl)-3 p-chlorophenyl-4 oxa-1 spiro[4,4-]nonane-one-2 by action of p-bromobenzene sulfonyl chloride in pyridine.

Then hydrochloric acid was added in order to obtain the desired hydrochloride, in solution in an ethanol-ether mixture.

Melting point=221°-223° C.

EXAMPLE 9

N-piperidinomethyl-3 p-chlorophenyl-4 oxa-1 spiro[4,5]decane-one-2 hydrochloride The process indicated in Example 1 was used taking as the starting compound cyclohexyl-p-chlorophenyl ketone (described in U.S. Pat. No. 3,308,159) in place of the cyclopentylphenyl ketone. Thus, β-cyclohexyl β-hydroxy chloro-4'-hydrocinnamic acid was formed which was converted into p-chlorophenyl-4 oxa-1 spiro[4,5]decane-one-2.

After formation of the corresponding acid (MP=156°-159° decomp.) using the technique described in Example 1, piperidine in solution in alcohol was added to give N-piperidinomethyl-3 p-chlorophenyl-4 oxa-1 spiro[4,5]decane-one-2 which was transformed into the hydrochloride thereof by action of hydrochloric acid in a mixture of ethanol-diethyl ether.

Melting point=214°-216° C. (decomp.).

EXAMPLE 10

N-piperidinomethyl-3 p-chlorophenyl-4 oxa-1 spiro[4,5]-decane hydrochloride

The process indicated in Example 6 was used, using N-piperidinomethyl-3 p-chlorophenyl-4 oxa-1 spiro[4,5]-decane-one-2 which was added slowly to a suspension of lithium-aluminum hydride in anhydrous tetrahydrofuran.

The amino-diol obtained was converted into N-piperidinomethyl-3 p-chlorophenyl-4 oxa-1 spiro[4,5]-decane by the action of p-bromobenzene sulfonyl chloride in pyridine.

The hydrochloride was obtained by the usual technique by action of hydrochloric acid in an ethanol-diethyl ether mixture.

Melting point=281°-283° C.

EXAMPLE 11

N-piperidinomethyl-3 p-tolyl-4 oxa-1 spiro[4,5]decane-one-2 hydrochloride

This product was obtained using the process of Example 9 but using cyclohexyl p-tolyl ketone as the starting compound. The N-piperidinomethyl-3 p-tolyl-4 oxa-1 spiro-[4,5]decane-one-2 was transformed into the hydrochloride thereof by the action of hydrochloric acid in an ethanol-diethyl ether mixture.

Melting point = 214°-216° C. (decomp.).

EXAMPLE 12

N-piperidinomethyl-3 p-tolyl-4 oxa-1 spiro[4,5]decane hydrochloride

This was carried out as indicated in Example 6 using N-piperidinomethyl-3 p-tolyl-4 oxa-1 spiro[4,5]decane-one-2 which was added slowly to a suspension of lithium aluminum hydride in anhydrous tetrahydrofuran to form the corresponding amino-diol.

The N-piperidinomethyl-3 p-tolyl-4 oxa-1 spiro[4,5]-decane was obtained from the amino-diol by the action of p-bromobenzene sulfonyl chloride in pyridine.

The hydrochloride was then prepared in the usual manner with hydrochloric acid and then extraction with a solvent composed of a ethanol-diethyl ether mixture.

Melting point = 283°-286° C. (decomp.)

What is claimed is:

1. Spiro derivatives of the general formula (I):

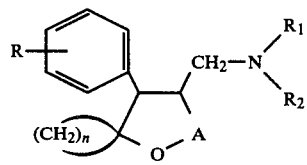

(I)

wherein R is a hydrogen atom, a halogen atom, an alkyl group or an alkoxy group; $R_1$ and $R_2$, which may be the same or different, represent a hydrogen atom, an alkyl group or together form a nitrogen-containing 5- or 6-membered heterocyclic ring in which the remaining atoms of said ring are carbon atoms; A represents a >$CH_2$ group or a >CO group; and n is 4 or 5 and the pharmaceutically acceptable acid addition salts thereof.

2. The spiro derivatives of claim 1, wherein A represents a >CO group, and R is a hydrogen atom, a halogen atom or a methyl group.

3. The spiro derivatives of claim 1, wherein A is a >$CH_2$ group, and R is a hydrogen atom, a halogen atom or a methyl group.

4. The spiro derivatives of claim 2, selected from the group consisting of (dimethylaminomethyl)-3 phenyl-4 oxa-1 spiro[4,4]nonane-one-2, (dimethylaminomethyl)-3 phenyl -4 oxa-1 spiro[4,5]decane-one-2, (dimethylaminomethyl)-3 (p-tolyl)-4 oxa-1 spiro[4,5]decane-one-2, (dimethylaminomethyl)-3 p-chlorophenyl-4 oxa-1 spiro[4,4]nonane-one-2, N-piperidinomethyl-3 p-chlorophenyl-4 oxa-1 spiro[4,5]-decane-one-2, N-piperidinomethyl-3 p-tolyl-4 oxa-1 spiro-[4,5]decane-one-2.

5. The spiro derivatives of claim 3, selected from the group consisting of (dimethylaminomethyl)-3 phenyl-4 oxa-1 spiro[4,5]decane, (dimethylaminomethyl)-3 p-chlorophenyl-4 oxa-1 spiro[4,4]nonane, N-piperidinomethyl-3 p-chlorophenyl-4 oxa-1 spiro[4,5]-decane and N-piperidinomethyl-3 p-tolyl-4 oxa-1 spiro[4,5]decane.

6. The spiro derivative of claim 1, wherein the heterocyclic ring is a pyrrolyl group, a pyrrolidinyl group or a piperidinyl group.

7. A pharmaceutical composition for treatment of depression comprising an anti-depression effective amount of a spiro derivative of claim 1, 2, 3, 4 or 5, as an active ingredient, along with a pharmaceutically acceptable carrier or diluent.

8. A pharmaceutical composition useful as an antiarrhythmic agent comprising an effective amount to treat arrhythmia of a spiro derivative of claim 1, 2, 3, 4 or 5, as an active ingredient, along with a pharmaceutically acceptable carrier or diluent.

* * * * *